United States Patent [19]
Prakash et al.

[11] Patent Number: 5,654,484
[45] Date of Patent: Aug. 5, 1997

[54] POLYAMINE DERIVATIVES AS ANTINEOPLASTIC AGENTS

[75] Inventors: Nellikunja J. Prakash, Cincinnati; David M. Stemerick, Fairfield; Michael L. Edwards, Cincinnati, all of Ohio

[73] Assignee: Merrell Pharmaceuticals Inc., Cincinnati, Ohio

[21] Appl. No.: 457,247

[22] Filed: Jun. 1, 1995

Related U.S. Application Data

[63] Continuation of Ser. No. 292,555, Aug. 18, 1994, abandoned, which is a continuation of Ser. No. 92,277, Jul. 15, 1993, abandoned, which is a continuation of Ser. No. 982,276, Nov. 25, 1992, abandoned, which is a continuation of Ser. No. 825,451, Jan. 24, 1992, abandoned, which is a continuation of Ser. No. 684,446, Apr. 11, 1991, abandoned, which is a continuation of Ser. No. 608,598, Oct. 31, 1990, abandoned, which is a continuation of Ser. No. 295,617, Jan. 10, 1989, abandoned, which is a continuation-in-part of Ser. No. 106,197, Oct. 8, 1987, abandoned.

[51] Int. Cl.$^6$ .................................................. C07C 211/00
[52] U.S. Cl. ............................................. 564/511; 564/512
[58] Field of Search ..................................... 564/511, 512, 564/564

[56] References Cited

FOREIGN PATENT DOCUMENTS

| | | |
|---|---|---|
| 0270349 | 6/1988 | European Pat. Off. . |
| 0349224 | 1/1990 | European Pat. Off. . |

*Primary Examiner*—C. Warren Ivy
*Assistant Examiner*—Raymond Covington
*Attorney, Agent, or Firm*—Louis J. Wille; David M. Stemerick

[57] ABSTRACT

The present invention relates to a method for the treatment of patients suffering from certain neoplastic disease states which comprises administering a therapeutically effective amount of a compound of the formula:

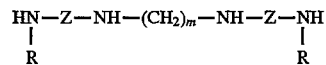

wherein m is an integer 6 to 9, Z is a saturated ($C_2$–$C_6$) alkylene moiety, each R group independently is hydrogen, methyl, ethyl, or n-propyl except that both R groups cannot be hydrogen when Z is a straight chain; or a pharmaceutically acceptable acid addition salt thereof. Said treatment can optionally comprise conjunctive therapy with a polyamine oxidase inhibitor. The invention also relates to certain novel polyamine derivatives.

5 Claims, No Drawings

POLYAMINE DERIVATIVES AS ANTINEOPLASTIC AGENTS

This is a continuation of application Ser. No. 08/292,555, filed Aug. 18, 1994 now abandoned; which is a continuation of application Ser. No. 08/092,277, filed Jul. 15, 1993, now abandoned; which is a continuation of application Ser. No.07/982,276, filed Nov. 25, 1992, now abandoned; which is a continuation of application Ser. No. 07/825,451, filed Jan. 24, 1992, now abandoned; which is a continuation of application Ser. No. 07/684,446 filed Apr. 11, 1991, now abandoned; which is a continuation of application Ser. No. 07/608,598, filed Oct. 31, 1990, now abandoned; which is a continuation of application Ser. No. 07/295,617, filed Jan. 10, 1989, now abandoned; which is a continuation in part of application Ser. No. 07/106,197 filed Oct. 8, 1987, now abandoned; which is herein incorporated by reference.

BACKGROUND OF THE INVENTION

Neoplastic disease states in humans are recognized throughout the world as being serious and sometimes life-threatening conditions. These neoplastic diseases, which are characterized by rapidly-proliferating cell growth, have been and continue to be the subject of worldwide research efforts directed toward the identification of therapeutic agents which are effective in the treatment of patients suffering therefrom. Effective therapeutic agents can be characterized as those which prolong the survivability of the patient, which inhibit the rapidly-proliferating cell growth associated with the neoplasm, or which effect a regression of the neoplasm. Research in this area is primarily focused toward identifying agents which would be therapeutically effective in humans. Typically, compounds are tested for antineoplastic activity in small mammals, such as mice, in experiments designed to be predictive of antineoplastic activity not only in those animals but also in humans against specific neoplastic disease states.

It is well known that naturally occurring polyamines, such as spermine and spermidine, play a role in cell growth and proliferation. These naturally occurring polyamines are found in animal cells and are produced in a biosynthetic pathway involving putrescine as a precursor. Putrescine is formed by a decarboxylation of ornithine by ornithine decarboxylase (ODC).

It has now been found that certain polyamine derivatives are effective therapeutic agents when administered to an animal suffering from certain neoplastic disease states.

SUMMARY OF THE INVENTION AND DETAILED DESCRIPTION

This invention relates to methods of use of certain polyamine derivatives in the treatment of patients suffering from certain neoplastic disease states and to pharmaceutical compositions containing these polyamine derivatives. The invention also relates to certain novel polyamine derivatives.

More specifically, this invention relates to a method for the treatment of patients suffering from certain neoplastic disease states which comprises administering a therapeutically effective amount of a compound of the formula (I):

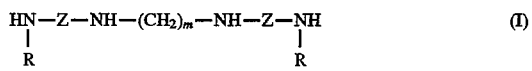

wherein m is an integer of from 6 to 9, Z is a saturated $(C_2-C_6)$ alkylene moiety, each R group independently is hydrogen, methyl, ethyl, or n-propyl except that both R groups cannot be hydrogen when Z is a straight chain; or a pharmaceutically acceptable acid addition salt thereof.

Said treatment can optionally comprise conjunctive therapy with a polyamine oxidase inhibitor.

As indicated above, the center alkylene moiety (i.e., "$(CH_2)_m$") of compounds of the formula (I) is a saturated, straight-chain hydrocarbylene radical comprising 6 to 9 carbon atoms. Preferred compounds for this method of use are those for which "m" is 7 or 8. As used herein, the term "Z" is understood to mean a saturated hydrocarbylene radical of straight or branched-chain configuration comprising 2 to 6 carbon atoms including, but not limited to, —$CH_2CH_2$—, —$CH_2CH_2CH_2$—, —$CH_2(CH_2)_2CH_2$—, —$CH_2(CH_2)_3CH_2$—, —$CH_2(CH_2)_4CH_2$—, —$CH(CH_3)CH_2$—, —$CH(CH_3)CH_2CH_2$—, and the like.

Compounds of the formula (I) can be used according to the present invention as pharmaceutically acceptable acid addition salts thereof. The term "pharmaceutically acceptable acid addition salt" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. The hydrochloric acid addition salts are preferred. The selection and preparation of pharmaceutically acceptable non-toxic acid addition salts are within the ability of one of ordinary skill in the art utilizing procedures and techniques well known and appreciated in the art.

In general, the compounds of formula (I) may be prepared by chemical reactions analogously known in the art, such as that described in U.S. patent application Ser. No. 010,380, filed Feb. 3, 1987, now abandoned, which is incorporated herein by reference. The choice of any specific route of preparation is dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (I).

A preferred route for the synthesis of compounds of the formula (I) wherein Z is —$CH_2CH_2CH_2$—, but also applicable by analogy for other compounds of formula (I) wherein Z is an alkyl-substituted propylene group (such as —$CH(CH_3)CH_2CH_2$—), is presented in Reaction Scheme A.

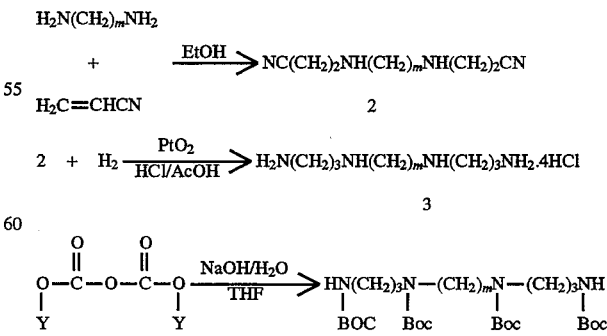

Reaction Scheme A

-continued

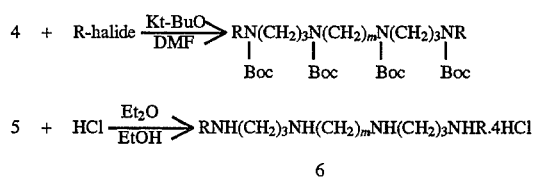

6 wherein m and R are as defined in formula (I), Boc is the t-butoxycarbonyl protecting group, and Y is tert-butyl.

The initial step of this process entails an N-alkylation of the appropriate diamine with 2 equivalents of acrylonitrile by heating reactants, either in a suitable solvent or neat, according to standard conditions well known in the art. The resulting cyano derivatives (2) are chemically reduced by reaction with hydrogen in the presence of a catalyst ($PtO_2$) in a suitable solvent, such as acetic acid containing 8 equivalents of hydrochloric or hydrobromic acid, to produce the resulting hydrohalic salts according to standard procedures well known in the art. Of course, other reducing sytems, e.g., reduction with lithium aluminum hydride, may also be utilized to produce compounds of formula (3). Following the preparation of these compounds the hydrohalic salts are neutralized with base and the nitrogen atoms are protected, preferably with di-t-butyldicarbonate according to standard operating conditions well known in the art. The tetra N-protected amines (4) are alkylated by reacting (4) with the appropriate alkyl halides (chloro or bromo) in the presence of potassium butoxide according to standard alkylation procedures well known in the art. When it is desired to provide compounds of the formula (I) wherein both R groups are the same, about 3 equivalents of the alkyl halide is reacted. When it is desired to provide compounds of the formula (I) wherein the R groups are not the same, monosubstitution of compounds of formula (4) is effected by reacting about 1 to about 1.5 equivalents of the alkyl halide with subsequent isolation of the mono-substituted compound according to standard procedures well known in the art and optionally further reacting the monosubstituted compound with the desired different alkyl halide. Following alkylation the N-protective groups of compound (5) are removed by standard procedures, e.g., treatment with acid, preferably HCl, in the presence of a suitable solvent or solvent system, e.g., diethyloxide in ethanol, to obtain the desired products (6).

Alternatively, compounds of formula (3) and their otherwise prepared homologs may be subjected to a reductive alkylation using an appropriate aldehyde. The reduction is effected by hydrogenation in the presence of $PtO_2$ or sodium cyanoborohydride according to well known procedures. This procedure does not require protection of the nitrogen atoms of the intermediates.

A preferred route for the preparation of compounds of formula (I) wherein Z is —$CH_2(CH_2)_2CH_2$—, but which is also applicable by analogy to those compounds wherein Z is any straight chain, is presented in Reaction Scheme B.

Reaction Scheme B

Reaction Scheme B

-continued

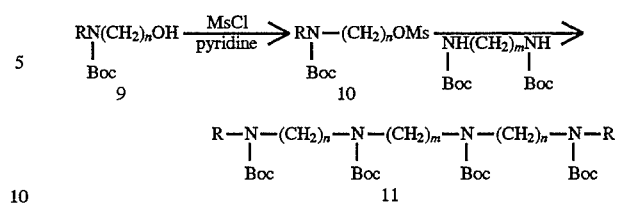

wherein m is as defined for formula (I), n is an integer 2 to 6 describing a straight chain alkylene moiety, Boc is the t-butoxycarbonyl protecting group, R is as defined in formula (I), Ms is mesyl and $R_1$ is hydrogen, methyl or ethyl.

This synthesis is initiated by reductive alkylation techniques well known in the art using an amino alcohol (7) and an appropriate aldehyde to form R- substituted amino alcohols (8). The nitrogen atom is protected, preferably with di-t-butyldicarbonate, according to standard operating conditions well known in the art, to yield the N-protected amino alcohols (9) which are converted to their mesylates (10) by known reaction conditions, e.g., reaction with mesylchloride in the presence of pyridine, preferably in a solvent such as $CH_2Cl_2$.

The mesylate is subjected to alkylation with an N-protected diamine (i.e., $BocNH(CH_2)_m NHBoc$) in the presence of potassium t-butoxide in a solvent such as DMF. The so-produced tetra N-protected tetramines (11) are deprotected as in Scheme A. In essence the foregoing reductive alkylation, N-protection, mesylation, alkylation and deprotection procedures all employ techniques and reaction conditions which are well known in the art.

In those instances wherein it is desired to prepare compounds of formula (I) wherein Z is —$CH_2$—$CH_2$—, it is preferred to employ Reaction Scheme C to obtain the necessary intermediates (14) which could be subjected to the alkylation procedures discussed above in Scheme A.

Reaction Scheme C

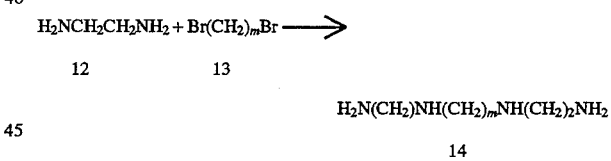

wherein m is as defined in formula (I).

The foregoing N-alkylation entails the reaction of an appropriate dihaloalkane (13) with excess quantities (10×) of ethylene diamine (12) by heating the reactants at reflux temperatures in a suitable solvent, e.g., ethanol. Preparation of the final products bearing the desired R substituents on the terminal nitrogen atoms of the intermediates (14).may be effected by N-protection, alkylation with the appropriate alkyl halide, and deprotection in an analogous manner to that described for Reaction Scheme A. Preferably, the alkylation can be carried out by the reductive alkylation procedures without N-protection as alternatively described for Reaction Scheme A.

Based upon standard laboratory experimental techniques and procedures well known and appreciated by those skilled in the art, as well as upon comparisons with compounds of known usefulness, the compounds of formula (I) can be used in the treatment of patients suffering from those neoplastic disease states which are dependent upon polyamine biosynthesis for their growth. Such neoplastic diseases include:

leukemias, including but not limited to acute lymphoblastic, chronic lymphocytic, acute myloblastic and chronic mylocytic; carcinomas, including but not limited to those of the cervix, esophagus, stomach, small intestines, colon and lungs; sarcomas, including but not limited to oesteroma, osteosarcoma, lipoma, liposarcoma, hemangioma and hemangiosarcoma; melanomas, including amelanotic and melanotic; and mixed types of neoplasias such as, for example, carcinosarcoma, lymphoid tissue type, folicullar reticulum, cell sarcoma and Hodgkins Disease. Of course, one skilled in the art will recognize that not every compound of formula (I) will be effective against each of the neoplastic disease states, and that selection of the most appropriate compound is within the ability of one of ordinary skill in the art and will depend on a variety of factors including assessment of results obtained in standard animal tumor models.

As used herein, the term "patient" refers to a warm-blooded animal such as a mammal which is afflicted with a neoplastic disease state. It is understood that dogs, cats, rats, mice, horses, bovine cattle, sheep, and humans are examples of animals within the scope of the meaning of the term.

The term "neoplastic disease" as used herein refers to an abnormal state or condition characterized by rapidly proliferating cell growth or neoplasm such as a carcinoma, a sarcoma, a leukemia, and a melanoma.

Treatment of a patient afflicted with a neoplastic disease stage comprises administering to such patient an amount of a compound of the formula (I) which is therapeutically effective in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm. It is believed that prolonging the survivability of a patient, beyond being a significant advantageous effect in and of itself, also indicates that the growth of the neoplasm has been controlled.

In effecting treatment of a patient afflicted with a neoplastic disease state a compound of formula (I) can be administered parenterally in any manner which makes (I) bioavailable in effective amounts including for example, by intraperitoneal (i.p.), subcutaneous (s.c.), or intravenous (i.v.) injection. Administration by intravenous injection is preferred.

A therapeutically effective dose or amount can readily be determined by the attending diagnostician and is a function of a number of factors including, but not limited to, the species of mammal, its size, age and general health, the specific neoplasm involved, the degree of involvement, the stage of development of the neoplasm, the compound selected and mode of administration, the bioavailability characteristics of the preparation administered, the dose regimen selected, and use of concomitant medication. The correct amount for any specific situation can be readily determined by those skilled in the art using conventional range finding techniques and analogous results observed under other circumstances. A therapeutically effective amount of (I) will vary from about 1 milligram per kilogram of body weight per day (mg/kg/day) to about 500 mg/kg/day and preferably will be about 5 mg/kg/day to about 50 mg/kg/day. It is believed that compounds of the formula (I) administered at the above doses to a patient suffering from a neoplastic disease are therapeutically effective in controlling the growth of one or more neoplastic disease states or in prolonging the survivability of the patient beyond that expected in the absence of such treatment.

A preferred embodiment of the present invention, relating to a method of treatment of patients suffering from a neoplastic disease state, comprises administering to said patient a therapeutically effective amount of a compound of the formula (I) in conjunctive therapy with an effective amount of a polyamine oxidase (PAO) inhibitor. The term "conjunctive therapy" contemplates coadministration of (I) along with a PAO inhibitor at essentially the same time, or treatment of the patient with a PAO inhibitor prior to or after treatment with (I). The PAO inhibitor is administered in an amount effective in substantially inhibiting PAO in the patient. When a compound of the formula (I) and a PAO inhibitor are administered in conjunctive therapy the PAO inhibitor may produce an additive or synergistic effect with (I). Thus, the dose of (I) required to produce a therapeutic effect in the patient may be less when administered in conjunctive therapy with an effective amount of a PAO inhibitor than that required when (I) is administered alone.

Various PAO inhibitors can be used including, but not limited to, N,N'-bis(2,3-butadienyl)-1,4-butanediamine, $\underline{N}$-(2,3-butadienyl)-N'-(methyl)-1,4-butanediamine, or pharmaceutically acceptable acid addition salts thereof as described in U.S. Pat. No. 4,551,550 which is incorporated herein by reference. N,N'-bis(2,3-butadienyl)-1,4-butanediamine is preferred as the PAO inhibitor for conjunctive therapy.

In effecting conjunctive therapy of a patient afflicted with a neoplastic disease state the PAO inhibitor can be administered parenterally in any manner which makes the PAO inhibitor bioavailable in effective amounts including, for example, by intraperitoneal (i.p.), subcutaneous (s.c.) or intravenous (i.v.) injection. Administration by intravenous injection is preferred.

An effective dose of the PAO inhibitor can readily be determined by the attending diagnostician and is a function of a number of factors including, but not limited to, the species of mammal, its size, age and general health, the specific neoplasm involved, the degree of involvement, the stage of development of the neoplasm, the mode of administration, the bioavailability characteristics of the compounds and preparation administered, the dose regimen selected, and use of concomitant medication. The correct amount of any specific situation can be readily determined by those skilled in the art using conventional range finding techniques and analogous results observed under other circumstances. An effective amount of a PAO inhibitor will vary from about 0.1 mg/kg/day to about 100 mg/kg/day and preferably will be about 1 mg/kg/day to about 10 mg/kg/day.

Another embodiment of the present invention relates to pharmaceutical compositions for parenteral administration for compounds of the formula (I). These pharmaceutical compositions comprise a therapeutically effective amount of one or more compounds of the formula (I) in an admixture with one or more pharmaceutically acceptable excipients, with or without, an effective amount of a PAO inhibitor. Such compositions are prepared in conventional manner well known in the art of pharmaceutical science. The amounts of the active ingredient(s) in a unit dosage form and the dosage regimen are adjusted to provide a sustained pharmacologic effect at the dose regimen selected.

Pharmaceutically acceptable excipients are substances that are chemically inert to the active compound(s) and have no detrimental side effects or toxicity to mammals under the conditions of use. Suitable excipients include solvents such as water, alcohol, and propylene glycol, surface active agents, suspending agents, lubricants, flavors, colorants, and the like. Such carriers and excipients are known to those in the art and are disclosed, for example, in texts such as *Remington's Pharmaceutical Manufacturing*, 13th Edition, Mack Publishing Co., Easton, Pa. (1965).

Injectable dosage forms of a solution or suspension of (I) can be prepared, for example, in a physiologically acceptable diluent with a pharmaceutical carrier which can be a sterile liquid such as water and oils with or without the addition of a surfactant and other pharmaceutically acceptable adjuvants and with or without a PAO inhibitor. Illustrative of oils which can be employed in these preparations are those of petroleum, animal, vegetable or synthetic origin, for example, peanut oil, soybean oil and mineral oil. In general, water, saline, aqueous dextrose and related sugar solution ethanols and glycols such as propylene glycol or polyethylene glycol are preferred liquid carriers, particularly for injectable solutions.

As is well known in the art of pharmaceutical inventions wherein generic classes of compounds are involved, certain subgeneric and certain specific compounds are more efficient in their end-use applications than other members of the generic class. In this invention, those compounds having a center alkylene chain of 6 to 8 carbon atoms are preferred, particularly those having seven or eight carbon atoms. Also preferred are those compounds wherein Z has two, three or four carbon atoms, with —$CH_2CH_2CH_2$— and —$CH(CH_3)CH_2CH_2$— being most preferred. In all instances it has been shown that the symmetrical compounds are preferred. Compounds for which each R is independently methyl or ethyl are preferred for this method of use and compounds for which both R groups are methyl or both R groups are ethyl are preferred. Compounds for which both R groups are the same moiety are generally preferred.

The following compounds are preferred in the method of use described by the present invention:

N,N'-bis(3-(ethylamino)propyl)-1,8-octanediamine;
N,N'-bis(3-aminobutyl)-1,8-octanediamine;
N,N'-bis(3-(methylamino)propyl)-1,8-octandiamine;
N,N'-bis(3-(propylamino)propyl)-1,8-octanediamine; and
N-(3-(aminopropyl)-N'-3-(ethylamino)propyl-1,8-octanediamine;
N,N'-bis[3-(methylamino)butyl]-1,7-diaminoheptane;
N,N'-bis[3-(ethylamino)butyl]-1,7-diaminoheptane;
N,N'-bis[3-(ethylamino)propyl]-1,7-diaminoheptane.
Of these compounds, N,N'-bis(3-(ethylamino)propyl)-1,8-octanediamine, N,N'-bis(3-(methylamino)propyl)-1,8-octanediamine, N,N'-bis[3-(methylamino)butyl]-1,7-diaminoheptane, N,N'-bis[3-(ethylamino)butyl]-1,7-diaminoheptane and N,N'-bis[3-(ethylamino)propyl]-1,7-diaminoheptane are most preferred.

Certain compounds of the formula (I) are novel. These novel compounds represent another embodiment of the present invention and are described by the formula (Ia):

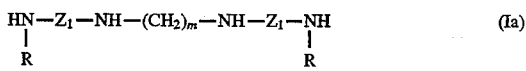

wherein m and R are as described above for compounds of formula (I) and $Z_1$ is a saturated ($C_2$–$C_6$) branched chain alkylene moiety; or a pharmaceutically acceptable acid addition salt thereof. These compounds are useful as antineoplastic agents as described above for compounds of formula (I). As used herein, the term $Z_1$ is understood to mean a saturated hydrocarbylene radical of branched chain configuration comprising 2 to 6 carbon atoms including with its scope, but not limited to, *—$CH(CH_3)CH_2CH_2$— and *—$CH(C_2H_5)CH_2CH_2$— wherein * indicates the point of attachment of the terminal amine. Compounds of the formula (Ia) can exist as free amines or as pharmaceutically acceptable acid addition salts thereof as described above for compounds of formula (I).

In general, compounds of the formula (Ia) can be prepared in an analogous manner to that described in Reaction Scheme D.

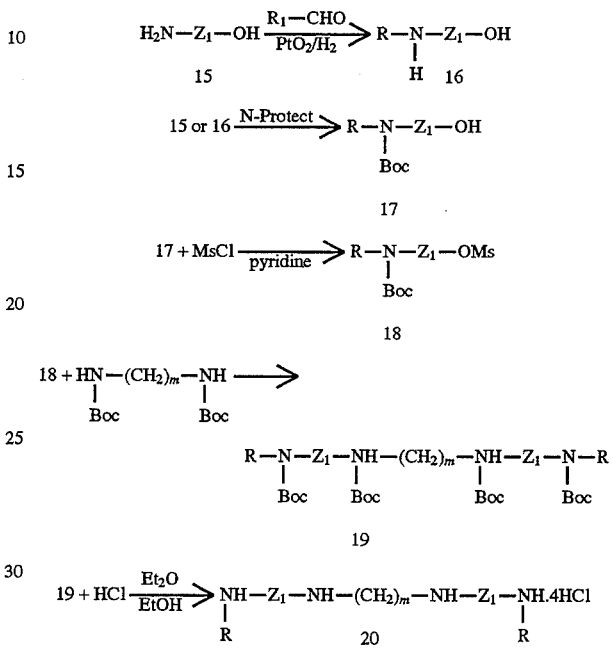

wherein m, R and $Z_1$ are as generically defined for formula (Ia), $R_1$ is hydrogen, methyl or ethyl.

The appropriate primary amino alcohol (15) containing a branched chain hydrocarbylene moiety (i.e., $Z_1$) is prepared by standard procedures well known in the art. If desired, the primary amine can at this point be converted to a secondary amine (16), by a reductive alkylation with the appropriate aldehyde. The amino alcohol is reacted as described in Reaction Scheme A by standard conditions well known in the art to effect protection of the amines with an appropriate N-protecting group such as Boc (17). The mesylates of the N-protected amino alcohols (18) are prepared and are alkylated with the appropriate N-protected diamine (i.e., BocNH($CH_2$)$_m$NHBoc) using standard procedures well known in the art as discussed for Reaction Scheme B. The so-produced tetra N-protected tetramines (19) are deprotected as in Scheme A to yield compounds of the formula (Ia). In essence, the foregoing reductive alkylation, N-protection, mesylation, alkylation and deprotective procedures all employ techniques and reaction conditions which are well known in the art.

Where it is desired to provide a compound of the formula (Ia) wherein each R group is not the same, the substituted mesylates (18) are prepared separately and monoalkylation of the appropriate N-protected diamine (i.e., BocNH($CH_2$)$_m$NHBoc) is effected by reacting the diamine with about 1.0 to 1.5 equivalents of one of the mesylates (18) with subsequent isolation of the monosubstituted compound and optionally further reacting the monosubstituted compound with the desired different substituted mesylate (18).

In those instances in which it is desired to prepare compounds of the formula (Ia) wherein $Z_1$ is an alkyl-substituted propylene group such as *—CH(Q)$CH_2CH_2$— wherein Q is a saturated alkyl radical comprising 1 to 3 carbon atoms of straight or branched chain configuration, Reaction Scheme E can be used to obtain intermediates of the formula (25) which can be de-protected to yield primary diamines of the formula (26) or which can optionally be subjected to alkylation of the N-terminal groups in a manner analogous to that described in Reaction Scheme A prior to de-protection.

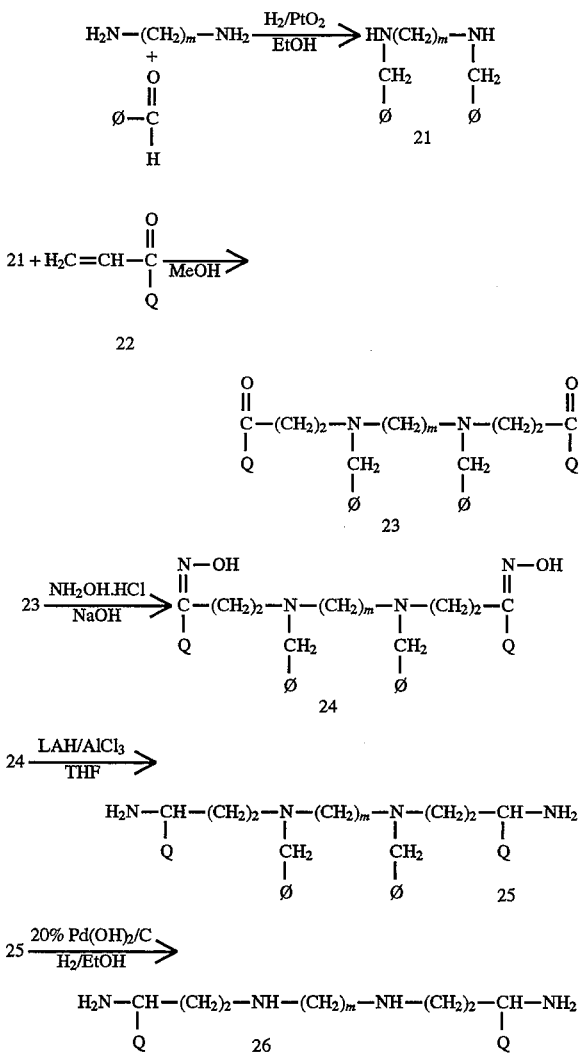

wherein m is as defined for formula (Ia), Ø is phenyl, and Q is as defined above.

The initial step of the process entails a reductive alkylation wherein the appropriate diamine is reacted with hydrogen gas and 2 equivalents of benzaldehyde in the presence of a catalyst such as $PtO_2$ to yield the N-protected diamine (21) under standard conditions well known in the art. The N-protected diamine (21) is then alkylated with 2 equivalents of the appropriate vinyl ketone (22) in a suitable solvent such as methanol using standard techniques. The resulting N-substituted diamine (23) is further reacted under standard conditions with hydroxylamine hydrochloride in the presence of base such as NaOH in a suitable solvent such as ethanol/water. The resulting oximes (24) are reduced to the corresponding N-protected di-primary amines (25) by reaction with lithium aluminum hydride (LAH) in the presence of Al $Cl_3$ in a suitable solvent such as THF according to standard procedures. Where the di-primary amine is desired as the final product, the N-protected di-primary amines (25) are de-protected by reaction with hydrogen gas in the presence of a suitable catalyst such as Pearlman's Catalyst (i.e., 20% $Pd(OH)_2$ on carbon) and a suitable solvent such as ethanol according to standard procedures. When secondary amines are desired as the amino-terminal groups of the final product, the N-protected di-primary amines (25) can be further alkylated with an appropriate aldehyde prior to deprotection in a manner analogous to that described for Reaction Scheme A.

Compounds of formula (Ia) wherein $Z_1$ is *—$CH(CH_3)$$CH_2CH_2$— or *—$CH(C_2H_5)CH_2CH_2$— are generally preferred in their end-use application. Compounds of formula (Ia) wherein each R group is the same moiety are also preferred. Compounds of formula (Ia) wherein each R group is methyl or ethyl are particularly preferred.

The following compounds of formula (Ia) are especially preferred embodiments of the present invention:
N,N'-bis(3-aminobutyl)-1,8-octanediamine;
N,N'-bis(3-aminopentyl)-1,8-octanediamine;
N,N'-bis[3-(methylamino)butyl]-1,7-diaminoheptane; and
N,N'-bis[3-(ethylamino)butyl]-1,7-diaminoheptane.

In order to illustrate the preparation of compounds of formulas (I) and (Ia), the following examples are provided. The examples are illustrative only and are not intended to limit the invention in any way. All temperatures are in degrees Celsius and the following abbreviations are used: (g) is grams, (mol) is moles, (ml) is milliliters, (l) is liters, (lb/in$^2$) is pounds per square inch, (TLC) is thin layer chromatography, (THF) is tetrahydrofuran, (DMF) is dimethylformamide, (mp) is melting point, (mm/Hg) is pressure expressed as millimeters of mercury, (bp) is boiling point.

EXAMPLE 1

N,N-Bis((3-methylamino)propyl)-1,8-octanediamine tetrahydrochloride

Step A: N,N'-Bis(2-(cyano)ethyl)-1,8-octanediamine

Dissolve 14.4 g (0.1 mol) of 1,8-diaminooctane and 14.5 ml (0.22 mol) of acrylonitrile in 100 ml of ethanol and reflux overnight. Remove the solvent at reduced pressure. Analysis showed the title compound to be >98% pure.

Step B: N,N'-Bis(3-(amino)propyl)-1,8-octanediamine tetrahydrochloride

Combine 14.4 g (0.057 mol) of the product of Step A, 200 ml of acetic acid, 30 ml of conc. HCl, and 1.2 g $PtO_2$ and treat the mixture with $H_2$ at 45 lbs/in$^2$ in a shaker flask until $H_2$ is no longer being reacted. Filter the mixture and remove the solvent at reduced pressure. 22.5 g of the title compound is obtained after purification. ($R_f$ is 0.17 for TLC on silica gel developed with 40% conc. ammonia/methanol).

Step C: 1,5,14,18-Tetra(t-butoxycarbonyl)-1,5,14,18-tetraazaoctadecane

Combine 22.5 g (0.052 mol) of the product of Step B with 8.83 g (0.22 mol) of NaOH, 100 ml $H_2O$ and 500 ml THF and stir until a homogenous solution is obtained. To this solution add 48.13 g (0.22 mol) of di-t-butyldicarbonate and stir the resulting mixture overnight. Pour the mixture into 1 l. of ethyl acetate, separate the organic layer, and dry over anhydrous $MgSO_4$. Remove the solvent at reduced pressure. Purify the residue by flash chromatography (silica gel), eluting with 25% ethyl acetate/hexane to yield 13.5 g of the title compound ($R_f$ is 0.28 for TLC on silica gel developed with 25% ethyl acetate/hexane).

Step D: 1,18-Bis(methyl)-1,5,14,18-tetra(t-butoxycarbonyl)-1,5,14,18-tetraazoctadecane Combine 4.3 g (0.0068 mol) of the product of Step C, 0.94 ml (0.015 mol) of iodomethane, 1.69 g (0.015 mol) of potassium t-butoxide, and 15 ml DMF and stir overnight. Remove the solvent at reduced pressure and dissolve the residue in 500 ml ethyl acetate and 200 ml of $H_2O$. Wash the organic layer with 100 ml $H_2O$ (2×) and dry over anhydrous $MgSO_4$. Remove the solvent at reduced pressure and purify the residue by flash chromatography (silica gel), eluting with 20% ethyl acetate/hexane to yield 4.4 g of the title compound ($R_f$ is 0.20 for TLC on silica gel developed with 20% ethyl acetate/hexane.)

Step E: N,N'-Bis(3-(methylamino)propyl)-1,8-octanediamine tetrahydrochloride

Dissolve 4.4 g (0.0065 mol) of the product of Step D in 3 ml ethanol and treat the solution with 50 ml of $2\underline{N}$ HCl in diethyl ether stirring overnight. Filter the resulting mixture and crystallize the residue from methanol/isopropanol/water (20/60/20,v/v/v) at reduced temperature. Filter and dry the product at 79° C. over $P_2O_5$ at 0.1 mmHg to yield 2.08 g of the title compound (mp>300° C.). Elemental analysis: calculated, C-44.44, H-9.79, N-12.86, Cl-32.80; Found C-44.44, H-9.82, N-12.95, Cl-32.59, 32.64.

EXAMPLE 2

N,N'-Bis(3-(ethylamino)propyl)-1,8-octanediamine tetrahydrochloride

Step A: 1,18-Bis(ethyl)-1,5,14,18-tetra(t-butoxycarbonyl)-1,5,14,18-tetraazaoctadecane Combine 9.5 g (0.0144 mol) of the product of Step C in Example 1, 2.91 g (0.026 mol) of potassium t-butoxide, and 45 ml of DMF and cool to 0° C. Add 2.1 ml (0.026 mol) of iodoethane and stir at 0° C. for 4 hours. Allow the mixture to warm slowly to room temperature and stir overnight. Remove the solvent at reduced pressure and partition the residue between 1400 ml ethyl acetate and 200 ml $H_2O$. Wash the organic layer with 100 ml $H_2O$ (2×) and dry over anhydrous $MgSO_4$. Remove the solvent under reduced pressure and purify the residue by flash chromatography (silica gel) eluting with 20% ethyl acetate/hexane to yield 3.3 g of the title compound ($R_f$ is 0.26 for TLC on silica gel developed with 20% ethyl acetate/hexane.)

Step B: N,N'-Bis(3-(ethylamino)propyl)-1,8-octanediamine tetrahydrochloride hemihydrate Dissolve 3.3 g (0.0046 mol) of the product of Step A in 7 ml ethanol and treat with 70 ml of $2\underline{N}$ HCl in diethyl ether stirring overnight. Filter the mixture and dry the residue at 70° C. at reduced pressure to yield 1.95 g of the title compound, mp>300° C. Elemental analysis: Calculated, C-46.09, H-10.10, N-11.95, Cl-30.24; Found C-46.23, H-9.94, N-12.11, Cl-29.99.

EXAMPLE 3

N-(3-Aminopropyl)-N'-(3-(ethylamino)propyl)-1,8-octanediamine tetrahydrochloride Step A: 1-Ethyl-1,5,14,18-tetra-(t-butoxycarbonyl)-1,5,14,18-tetraazaoctadecane Follow the procedure described in Step A of Example 2 to yield 2.5 g of the title compound after flash chromatography ($R_f$ is 0.17 for TLC on silica gel developed with 20% ethyl acetate/hexane).

Step B: N-(3-Aminopropyl)-N'-(3-(ethylamino)propyl)-1,8-octanediamine tetrahydrochloride Dissolve 2.5 g (0.0036 mol) of the product of Step A in 5 ml of ethanol and treat with 60 ml of $2\underline{N}$ HCl in diethyl ether stirring overnights. Filter the mixture and dry the residue to yield 1.35 g of the title compound, mp>300° C. Elemental analysis: Calculated, C-43.54, H-9.82, N-12.69, Cl-32.13; Found, C-43.43, H-9.60, 9.55; N-12.60, 12.62; Cl-32.30.

EXAMPLE 4

N,N'-Bis(3-aminobutyl)-1,8-Octanediamine

Step A: N,N'-Bis((phenyl)methyl)-1,8-octanediamine

Combine 14.4 g (0.1 mol) of 1,8-octanediamine, 20.3 ml (0.2 mol) of benzaldehyde, 0.3 g $PtO_2$ and 150 ml ethanol and treat the mixture with $H_2$ at 45 lb/in$^2$ in a shaker flask until no more gas is taken up. Remove the catalyst by filtration and remove the solvent at reduced pressure to yield the title compound.

Step B: N,N'Bis((3-oxo)butyl)-N,N'-bis((phenyl)methyl)-1,8-octanediamine

Dissolve the product obtained in Step A in 1400 ml of methanol and introduce 21.6 of methyl vinyl ketone on a stream of $N_2$ gas. Stir for 16 hours to yield the title compound.

Step C: N,N'-Bis((3-hydroxyimino)butyl)-N,N'-Bis-((phenyl)methyl)-1,8-octanediamine Combine 18.07 g hydroxylamine hydrochloride, 10.4 g of NaOH and 40 ml of $H_2O$ and add to the solution obtained in Step B. Reflux the mixture for 3 hours, then cool and evaporate the solvent. Pour the reaction mixture into 300 ml of ethyl acetate and wash with 300 ml $H_2O$. Wash the aqueous layer with 300 ml of ethyl acetate (2×). Combine the organic layers and dry over anhydrous $MgSO_4$. Remove the solvent at reduced pressure. Purify the product by flash chromatography (silica gel), eluting with ethyl acetate to yield 34.8 g of the title compound ($R_f$ is 0.42 for TLC on silica gel developed with ethyl acetate).

Step D: N,N'-Bis((3-Amino)butyl)-N,N'-Bis((phenyl)methyl)-1,8-octanediamine

Add 34.8 g of the product of Step C in 100 ml THF to 12.10 g (0.310 mol) of lithium aluminum hydride in 540 ml THF and reflux the mixture while stirring overnight. Cool the mixture and slowly add 15 ml $H_2O$ followed by 45 ml $1\underline{N}$ NaOH and stir the mixture for 6 hours. Filter the mixture to remove a white granular precipitate and remove the solvent at reduced pressure. Subject the residue to short path distillation to yield 17.0 g of the title compound (bp 230°–235° C. at 0.1 mmHg).

Step E: N,N'-Bis((3-amino)butyl)-1,8-octanediamine

Combine 5.0 g (0.01 mol) of the product of Step D, 0.5 g of 20% Pd(OH)$_2$ on carbon (Pearlman's Catalyst), and 50 ml of ethanol and treat the mixture with $H_2$ at 45 lb/in$^2$ in a shaker flask until no more gas is taken up. Remove the catalyst by filtration and remove the solvent at reduced pressure. Subject the residue to short path distillation to yield 1.59 g of the title compound (bp 145°–148° C. at 0.012

EXAMPLE 5

N,N'-Bis[3-(methylamino)butyl]-1,7-diaminoheptane tetrahydrochloride

Step A: N,N'-Bis[(phenyl)methyl]-1,7-heptanediamine

Combine 1,7-diaminoheptane (65.0 g, 0.5 mol), benzaldehyde (106 gm, 1 mol) and platinum oxide (PTO$_2$) [2.0 g] in ethanol (800 ml) and treat the mixture with hydrogen gas (45 lb/in$^2$) until the uptake of gas ceases. Remove the catalyst by filtration and remove the solvent in vacuo. Purify the residue by bulb to bulb distillation to yield 99.4 g of the title compound (bp 191°–195° C. @ 1.0 mm/Hg).

Step B: N,N'-Bis[(3-oxo)butyl]-N,N'-bis[(phenyl)methyl]-1,7-diaminoheptane

Dissolve N,N'-bis[(phenyl)methyl]-1,7-heptanediamine (9.3 g, 0.03 mol) in methanol (120 ml) and while stirring the mixture introduce methyl vinyl ketone (5.6 ml, 0.066 mol)

in a stream of nitrogen gas. Stir the mixture for 18 hours to yield the title compound.

Step C: N,N'-Bis[(3-hydroxyimino)butyl]-N,N'-bis[(phenyl)methyl]-1,7-diaminoheptane Cool the reaction mixture obtained in step B to 0° C. and to this mixture add a solution of hydroxylamine hydrochloride (4.38 g, 0.063 mol) and sodium bicarbonate (5.54 g, 0.066 mol) in water (40 ml). Stir the mixture at 0° C. for 30 minutes and then stir at ambient temperature for 2 hours. Remove the solvent in vacuo and partition the residue between water (200 ml) and dichloromethane (200 ml). Wash the aqueous layer 3 times with 200 ml of dichloromethane each time. Combine the organic layers and dry over anhydrous $MgSO_4$. Remove the solvent in vacuo to yield 14.4 g of the title compound. Rf is 0.53 for TLC on silica gel developed with ethyl acetate.

Step D: N,N'-Bis[3-(amino)butyl]-N,N'-bis[(phenyl)methyl]-1,7-diaminoheptane

Add a solution of N,N'-bis[(3-hydroxyimino)butyl]-N,N'-bis[(phenyl)methyl]-1,7-diaminoheptane (14.4 g, 0.03 mol) in THF (70 ml) to a mixture of lithium aluminum hydride (5.8 g, 0.15 mol) in THF (250 ml) and reflux the mixture overnight. Cool the mixture and quench slowly with water (5.8 ml), followed by 15% NaOH (5.8 ml), followed by water (17.4 ml). Filter the mixture and wash the filtrate 3 times with 100 ml of THF each time. Combine the organic layers and remove the solvent in vacuo to obtain 13.4 g of the title compound as a clear viscous oil. Rf is 0.33 for TLC on silica gel developed with 4% conc. ammonia in methanol.

Step E: 2,16-Bis(methyl)-1,5,13,17-tetra(t-butoxycarbonyl)-1,5,13,17-tetraazaheptadecane Combine N,N'-bis[3-(amino)butyl]-N,N'-bis[(phenyl)methyl]-1,7-diaminoheptane (13.4 g, 0.029 mol), Pearlman's Catalyst (2.0 g) and ethanol (90 ml) and treat the mixture with hydrogen gas at 45 lb/in² until gas uptake ceases. Remove the catalyst by filtration and remove the solvent in vacuo to obtain 7.7 g of N,N'-bis[3-(amino)butyl]-1,7-diaminoheptane (Rf is 0.37 for TLC on silica gel developed with 40% conc. ammonia in methanol). Dissolve the residue in dichloromethane (90 ml) and treat the mixture with di-t-butyldicarbonate (26.2 g, 0.12 mol) for 3 hours. Remove the solvent in vacuo and purify the residue by flash chromatography on silica gel eluting with 25% ethyl acetate in hexane to yield 17.1 g of the title compound as a clear oil. Rf is 0.35 for TLC on silica gel developed with 25% ethyl acetate in hexane.

Step F: 1,2,16,17-Tetramethyl-1,5,13,17-tetra(t-butoxycarbonyl)-1,5,13,17-tetraazaheptadecane Combine 2,16-bis(methyl)-1,5,13,17-tetra(t-butoxycarbonyl)-1,5,13,17-tetraazaheptadecane (8.5 g, 0.0126 mol) and sodium hydride (60% in oil) [1.21 g, 0.03 mol] in DMF (75 ml) and stir until hydrogen evolution ceases. To this mixture add methyl iodide (1.88 g, 0.03 mol) and stir for 2 hours. Remove the solvent in vacuo and partition the residue between ethyl acetate (400 ml) and water (200 ml). Dry the organic layer over anhydrous $MgSO_4$ and remove the solvent in vacuo. Purify the residue by flash chromatography on silica gel eluting with 22% ethyl acetate in hexane to yield 3.8 g of the title compound as a clear oil. Rf is 0.22 for TLC on silica gel developed with 20% ethyl acetate in hexane.

Step G: N,N'-Bis[3-(methylamino)butyl]-1,7-diaminoheptane tetrahydrochloride

Add 1N HCl in methanol (50 ml) to 1,2,16,17-tetramethyl-1,5,13,17-tetra(t-butoxycarbonyl)-1,5,13,17-tetraazaheptadecane (3.8 g, 0.0054 mol) and stir overnight. Remove the solvent in vacuo and recrystallize the residue two times from methanol/acetonitrile (40/60, v/v) to yield 0.74 g of the title compound as a white solid (mp 238°–9 ° C.). Rf is 0.31 for TLC on silica gel developed with 40% conc. ammonia in methanol.

EXAMPLE 6

N,N'-Bis[3-(ethylamino)butyl]-1,7-diaminoheptane tetrahydrochloride

Step A: 1,17-Diethyl-2,16-dimethyl-1,5,13,17-tetra(t-butoxycarbonyl)-1,5,13,17-tetraazaheptadecane Combine 2,16-bis(methyl)-1,5,13,17-tetra(t-butoxycarbonyl)-1,5,13,17-tetraazaheptadecane (8.5 g, 0.0126 mol), made as described in Example 5, and sodium hydride (60% in oil) [1.21 g, 0.03 mol] in DMF (75 ml) and stir until hydrogen evolution ceases. To this mixture add ethyl iodide (4.68 g, 0.03 mol) and stir for 2 hours. Remove the solvent in vacuo and partition the residue between ethyl acetate (400 ml) and water (200 ml). Dry the organic layer over anhydrous $MgSO_4$ and remove the solvent in vacuo. Purify the residue by flash chromatography on silica gel eluting with 22% ethyl acetate in hexane to yield 3.9 g of the title compound as a clear oil. Rf is 0.31 for TLC on silica gel developed with 20% ethyl acetate in hexane.

Step B: N,N'-Bis[3-(ethylamino)butyl]-1,7-diaminoheptane tetrahydrochloride

Add 1N HCl in methanol (50 ml) to 1,17-diethyl-2,16-dimethyl-1,5,13,17-tetra(t-butoxycarbonyl)-1,5,13,17-tetraazaheptadecane (3.9 g, 0.0054 mol) and stir overnight. Remove the solvent in vacuo and recrystallize the residue two times from methanol/acetonitrile (40/60, v/v) to yield 0.90 g of the title compound as a white solid (mp 249°–50 ° C.). Rf is 0.56 for TLC on silica gel developed with 40% conc. ammonia in methanol.

We claim:

1. A compound of the formula:

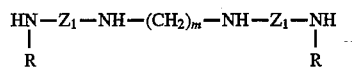

wherein m is an integer 6 to 8, $Z_1$ is a branched chain ($C_4$) alkylene moiety, and each R group independently is ethyl, or propyl; or a pharmaceutically acceptable acid-addition salt thereof.

2. The compound N,N'-bis(3-aminobutyl)-1,8-octanediamine.

3. The compound N,N'-bis[3-(ethylamino)butyl]-1,7-diaminoheptane.

4. A pharmaceutical composition in unit dosage form, which comprises (1) one or more pharmaceutically acceptable excipients, and (2) a therapeutically effective amount of a compound of the formula:

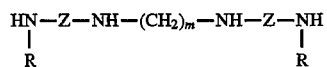

wherein m is an integer 6 to 8, Z is a saturated $C_4$ alkylene moiety, each R group independently is ethyl, or n-propyl except that both R groups cannot be hydrogen unless Z is a branched chain; or a pharmaceutically acceptable acid-addition salt thereof.

5. A pharmaceutical composition according to claim 4 which further comprises an effective amount of a polyamine oxidase inhibitor as an additional ingredient.

* * * * *